(12) United States Patent
Melsheimer et al.

(10) Patent No.: US 8,348,494 B2
(45) Date of Patent: Jan. 8, 2013

(54) VERTEBROPLASTY CEMENT MIXER INJECTOR DEVICE

(75) Inventors: Jeffry S. Melsheimer, Springville, IN (US); Meridith Cavett, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 13/470,632

(22) Filed: May 14, 2012

(65) Prior Publication Data

US 2012/0224452 A1 Sep. 6, 2012

Related U.S. Application Data

(63) Continuation of application No. PCT/US2010/061429, filed on Dec. 21, 2010.

(60) Provisional application No. 61/291,425, filed on Dec. 31, 2009.

(51) Int. Cl.
*B01F 15/02* (2006.01)
(52) U.S. Cl. .......................................... 366/184; 366/189
(58) Field of Classification Search .................. 366/184, 366/189, 256, 332, 139, 279, 347, 349
See application file for complete search history.

(56) References Cited

U.S. PATENT DOCUMENTS

| | | | | |
|---|---|---|---|---|
| 3,036,819 A | * | 5/1962 | Peterson | 206/221 |
| 3,144,966 A | * | 8/1964 | Cook | 222/136 |
| 4,676,406 A | * | 6/1987 | Frischmann et al. | 222/136 |
| 5,252,301 A | * | 10/1993 | Nilson et al. | 422/225 |
| 5,328,262 A | * | 7/1994 | Lidgren et al. | 366/139 |
| 5,779,356 A | * | 7/1998 | Chan | 366/139 |
| 6,676,664 B1 | | 1/2004 | Al-Assir | |
| 7,073,936 B1 | * | 7/2006 | Jonsson | 366/139 |
| 7,524,103 B2 | * | 4/2009 | McGill et al. | 366/189 |
| 2008/0212405 A1 | | 9/2008 | Globerman | |
| 2009/0057168 A1 | | 3/2009 | Smit | |
| 2009/0281549 A1 | | 11/2009 | Dixon | |

FOREIGN PATENT DOCUMENTS

EP 1466572 A2 10/2004

OTHER PUBLICATIONS

WIPO search report PCT/ISA/210 for PCT/US2010/061429 corresponding to WO2011082015, dated Jun. 14, 2011, 6 pages.*
WIPO preliminary opinon PCT/ISA/237 for PCT/US2010/061429 corresponding to WO2011082015, dated Jun. 14, 2011 same as the PCT/ISA/210 date, 9 pages.*

* cited by examiner

*Primary Examiner* — Tony G Soohoo
(74) *Attorney, Agent, or Firm* — Woodard, Emhardt, Moriarty, McNett & Henry LLP

(57) ABSTRACT

A system and apparatus for mixing and dispensing a composition, such as a vertebroplasty composition, is disclosed.

25 Claims, 12 Drawing Sheets

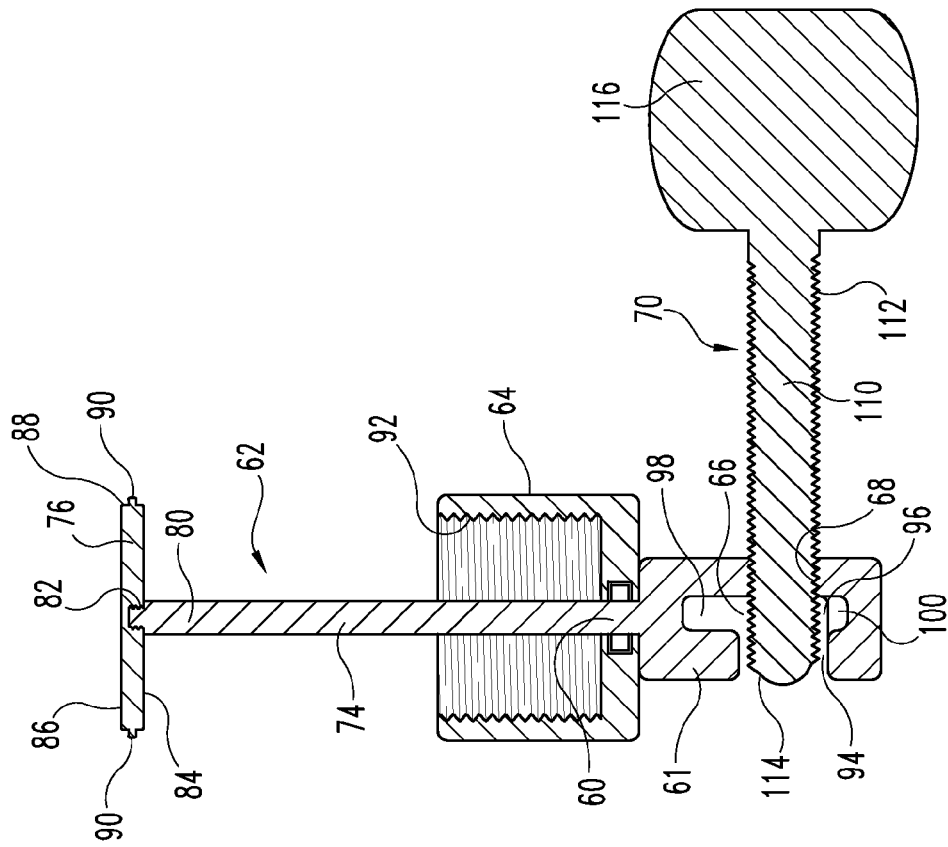
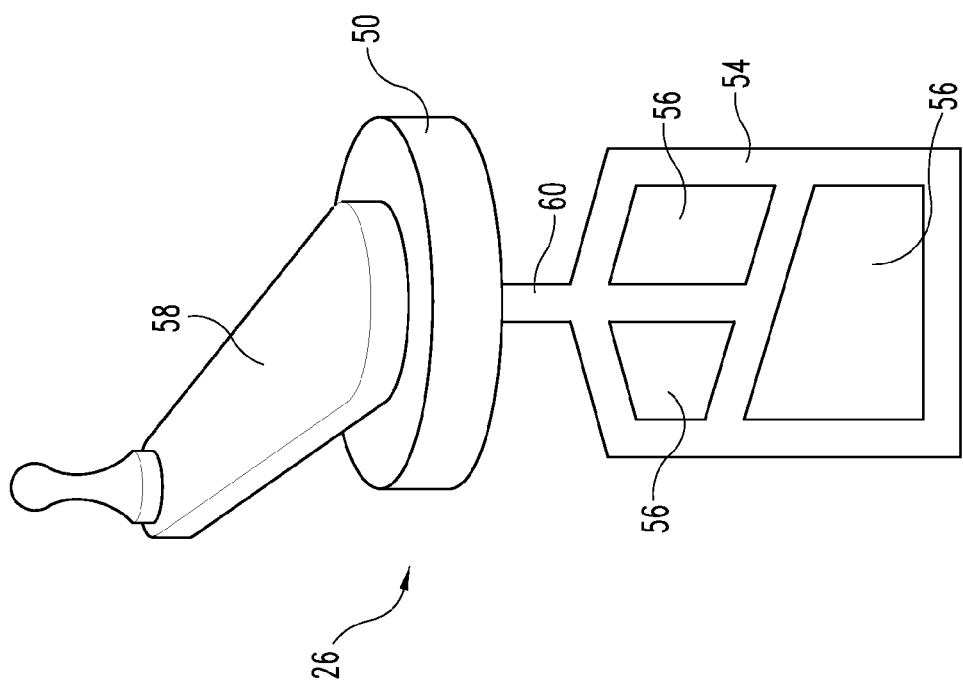
*Fig. 4*
*Fig. 3*

VERTEBROPLASTY CEMENT MIXER INJECTOR DEVICE

REFERENCE TO RELATED APPLICATIONS

This application is a continuation of International Application No. PCT/US2010/061429, filed Dec. 21, 2010, which claims the benefit of U.S. Provisional Application No. 61/291,425, filed Dec. 31, 2009, both entitled VERTEBROPLASTY CEMENT MIXER INJECTOR DEVICE, which are hereby incorporated by reference.

The present disclosure concerns devices for mixing and injecting compositions for treating conditions in bone. In particular, embodiments of devices for combining bone cement components and transferring the resulting cement to an injector and to a vertebroplasty site are disclosed.

BACKGROUND

In the field of vertebroplasty, a composition for supporting vertebral bone is injected into or around bone, e.g. by filling and/or covering internal or external cracks, holes or deteriorations in the natural tissue, so as to support the bone itself and/or surrounding tissue. Compositions such as bone cements of various ingredients are loaded into a syringe and injected through a needle and/or tubing to the bone or other site where the composition is desired. When an adequate volume of composition has been deposited, the injection(s) cease and the syringe (and needle and/or tubing if appropriate) are removed.

Generally, a number of different parts are required for preparing and injecting the composition. Compositions have been created in which a solid component (e.g. powdered cement or granulated polymer) is mixed with a liquid monomer to create the injectable composition. The solid and liquid components are combined in a mixing bowl or cup. When the injectable composition is ready, it is removed from the mixing bowl and placed in a syringe that is or will be connected to a tube or needle placed in the patient. The syringe plunger is then pressed to deposit the composition at the vertebroplasty site.

For example, kits featuring the Minimix and Duro-Ject devices sold by Cook Incorporated provide structure needed for vertebroplasty. A solid component is poured into the Minimix device, and a liquid monomer component is added. The components are mixed in the device for a period of time sufficient to develop a cement composition of appropriate homogeneity. A floor of the Minimix device is dropped below the level of an outlet port, and a syringe is connected to the outlet port. Drawing the syringe's plunger out fills the syringe with cement composition. The syringe is disconnected from the outlet port and is connected to another syringe or injector barrel without a plunger (via a stopcock in one example), and pushing in on the filled syringe's plunger moves cement composition from the syringe through the stopcock and into the injector barrel. The injector barrel is then disconnected from the stopcock and connected to a base of the Duro-Ject device, which has a threaded plunger for insertion into the injector barrel. Tubing that leads or will lead to the vertebroplasty site is connected to the other end of the injector barrel, and turning the threaded plunger forces cement composition out of the injector barrel and through the tubing to the vertebroplasty site.

The Duro-Ject and Minimix devices are quite effective in delivering compositions to vertebrae or other locations in the patient. Even so, they require a number of separate components and a number of separate actions in order to generate the composition and move it from a mixing station to an injecting station. Compositions used for vertebroplasty have been developed that cure in as little as around ten to fifteen minutes, and delays in preparing, transferring or injecting such compositions can result in lost composition, less- or ineffective vertebroplasty, or other difficulties. There is a need for devices that reduce the effort, time and number of devices required to prepare and place a vertebroplasty compositions.

SUMMARY

Among other things, there is disclosed a system for mixing and dispensing vertebroplasty composition, which can include a mixing container having a wall defining a chamber for mixing the composition and having a closed end, an open end, and a thread at or adjacent the open end. The system can also include an injector barrel for receiving cement dispensed from the container, and a dispensing component. The dispensing component, in some embodiments, has a base portion, a connecting portion compatible with the thread of the mixing container, a first plunger fixed to the base portion, and a threaded second plunger. When the dispensing component is connected with the mixing container through engagement of the connecting portion with the thread, the first plunger is in the chamber and contacting the interior surface of the wall of the mixing container. The threaded second plunger is threaded through and rotatable with respect to the handle and insertable into the injector barrel when the injector barrel is connected to the dispensing component.

In particular embodiments, the first plunger includes a shaft with first and second ends and a disc, with the first end fixed to the base portion of the dispensing component and the second end fixed to its disc, and the second end has an end surface that is exposed. The base portion can include an insertion area to which the injector barrel is connected, and the shaft may include a channel extending from the shaft's end surface through the shaft and base portion to the insertion area. The injector barrel can include a substantially cylindrical medial portion and have a first opening for accommodating the second plunger, a second opening at a tip portion, and a side hole between those first and second openings. When the injector barrel is connected to the insertion area of the base portion, such a side opening may communicate with the channel through the shaft and base member. At least one seal can be provided around one or both of the channel and side hole, so as to minimize leakage between the channel and injector barrel.

In some embodiments the closed end of the mixing container is movable toward the first plunger's disc when the first plunger is in the mixing container, so that the composition is forced from the mixing container into said channel. Alternatively, when the first plunger is in the mixing container, the disc can be movable with respect to the mixing container toward its closed end to force the composition into the channel. At least one of the end surface of the shaft and a surface of the disc adjacent that end surface may be at least partially concave and/or at least partially conical. The second plunger can be oriented substantially perpendicular to the first plunger.

In addition, the system can include a mixing attachment having a thread, a handle, and a paddle attached to and rotatable by that handle. When the mixing attachment is threaded with the thread of the mixing container, the paddle is within the chamber of the mixing container, and turning the handle turns the paddle to mix the components of the vertebroplasty composition in the container. The mixing container can include at least one outlet port adapted to connect to the injector barrel, and when the injector barrel is connected to the port, the closed end of the mixing container can be moved toward the disc of the first plunger, so that the composition is forced from the mixing container through the outlet portion and into the injector barrel. Alternatively, when the injector barrel is connected to the port, the first plunger's disc can be moved with respect to the mixing container toward the closed end to force the composition through the outlet port and into the injector barrel.

Also disclosed are embodiments of a system for mixing and dispensing a vertebroplasty composition, which has a mixing cup with an external wall, a closed end and an open end having an external thread, with the wall and closed end forming a mixing chamber for holding and mixing components of the vertebroplasty composition. A dispensing component having a base member firmly connectable to the open end of the mixing cup and a plunger fixed to the base member is also provided. The plunger has a shaft with first and second ends and a disc, with the first end fixed to the base portion and the second end fixed to the disc and with an end surface that is exposed. The dispensing component includes a channel extending from the end surface of the shaft through the shaft and base member to an outlet in the base member. A mixing component firmly connectable to the mixing cup can also be provided. The mixing component may have an axle, a handle connected to the axle directly or via a planetary or epicyclic gear set, and a paddle fixed to the other end of the axle, with the paddle being insertable into the mixing chamber of the mixing cup so that lateral edges of the paddle contact the wall of the mixing cup. When the mixing component is firmly connected to the mixing cup and components of the vertebroplasty composition are within the mixing chamber, turning the handle rotates the paddle to mix the composition's components.

In particular embodiments, the dispensing component includes a second plunger having a threaded shaft threadedly engaged with the base of the dispensing component. The plungers may be non-parallel or substantially perpendicular. An injector barrel having a first end insertable into the base member and a second tip end may also be provided. The first end may have a first opening that accommodates the second plunger, the second end may have a second opening, and the injector barrel may have a side hole intermediate those first and second openings that substantially aligns with the channel of the dispensing component when the injector barrel is inserted into the base member. In some embodiments, the closed end of the mixing cup is movable, and when the mixing cup is firmly connected to the dispensing component so that the plunger fixed to the base member is within the mixing chamber, the closed end is movable toward the plunger's disc. When vertebroplasty composition is within the mixing chamber and the injector barrel is inserted into the base member, movement of the closed end toward the disc forces vertebroplasty composition through the channel and into the injector barrel. Alternatively, the plunger fixed to the base member may be movable with respect to the mixing cup when within the mixing chamber, so that when vertebroplasty composition is within the mixing chamber and the injector barrel is inserted into the base member, movement of the disc toward the closed end forces vertebroplasty composition through the channel and into the injector barrel. At least one of the end surface of the plunger's shaft and a surface of the disc adjacent that end surface is at least partially concave or conical.

Also disclosed are vertebroplasty methods and methods of making and transferring composition or medicament for vertebroplasty treatment, which may include providing a dispensing component having a base, a first plunger immovably fixed to the base, and a second plunger threadedly connected to the base. Two or more components of the medicament or composition can be placed into a mixing cup and the components are then mixed. An injector barrel can be attached to the base of the dispensing component or to an exit port on the mixing cup. The first plunger of the dispensing component is inserted into the mixing cup to force at least some of the mixed medicament or composition through the plunger and base member, or through the exit port, and into the injector barrel. The second plunger threadedly connected to the base can then be used to force composition from the injector barrel, through a conduit and/or a needle, and to the vertebroplasty site.

These embodiments and others within the scope of the appended claims provide structure and methods that reduce the number of components and steps involved in a vertebroplasty procedure, making the procedure faster and easier for the physician and the patient. The amount of time required for injecting vertebroplasty compositions following their reconstitution is reduced, giving the physician more leeway in the procedure before the compositions become non-flowable or otherwise unusable. A principal embodiment provides a closed system, in which composition is mixed in a closed container and transferred through a closed conduit to an injector barrel, so that the composition can be injected to the vertebroplasty site from the injector barrel. That and other embodiments remove steps and apparatus from existing procedures. Other problems can be resolved by the structures and methods disclosed herein, as further indicated below.

BRIEF DESCRIPTION OF THE DRAWINGS

FIG. 3 is a side view of an embodiment of a mixing component part of an embodiment of a system for mixing and injecting vertebroplasty compositions as disclosed herein.

FIG. 4 is a cross-sectional view of the embodiment of a dispensing component as shown in FIG. 2.

DESCRIPTION OF THE ILLUSTRATED EMBODIMENTS

Figure 1:
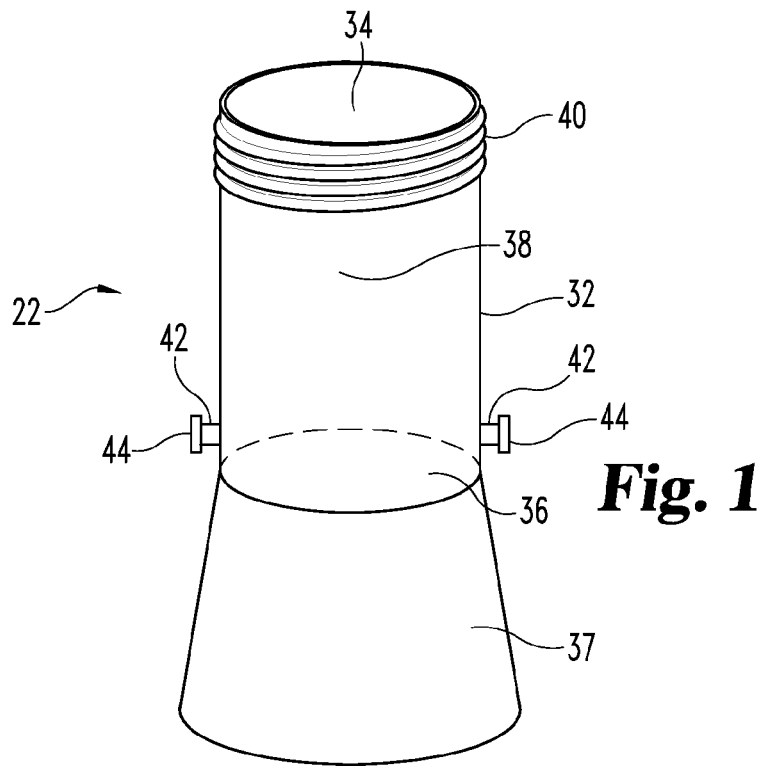
FIG. 1 is a side view of an embodiment of a mixing cup part of an embodiment of a system for mixing and injecting vertebroplasty compositions as disclosed herein.
Figure 2:
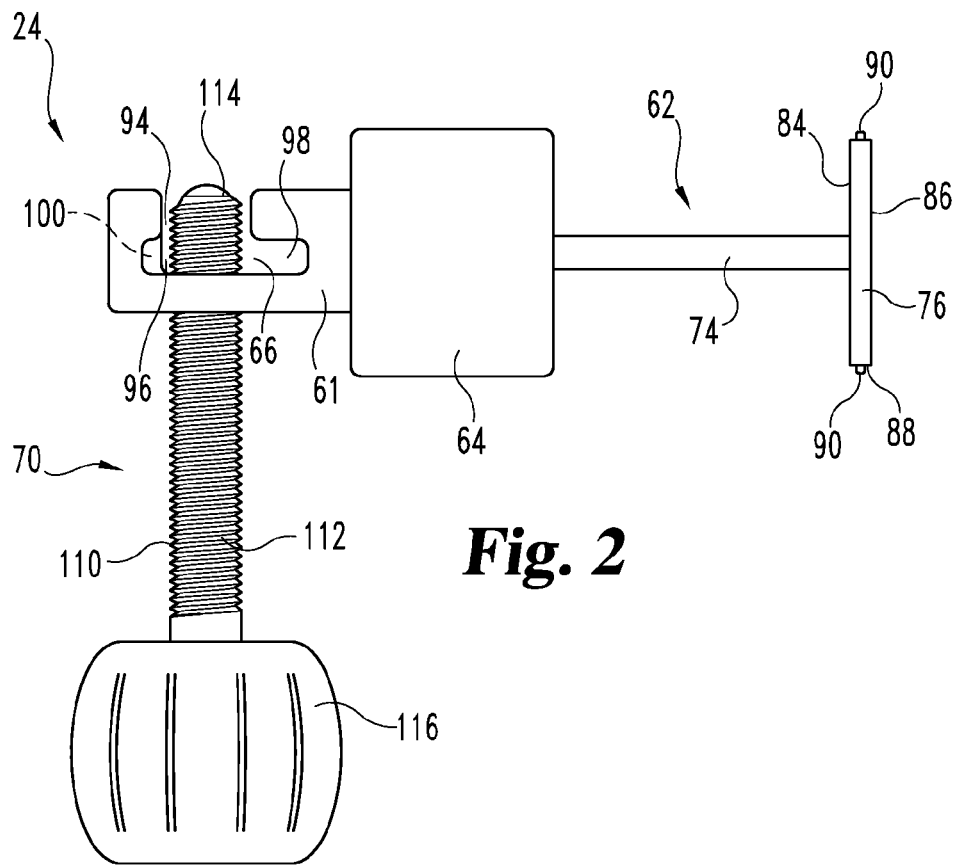
FIG. 2 is a side view of an embodiment of a dispensing component part of an embodiment of a system for mixing and injecting vertebroplasty compositions as disclosed herein.
Figure 5:
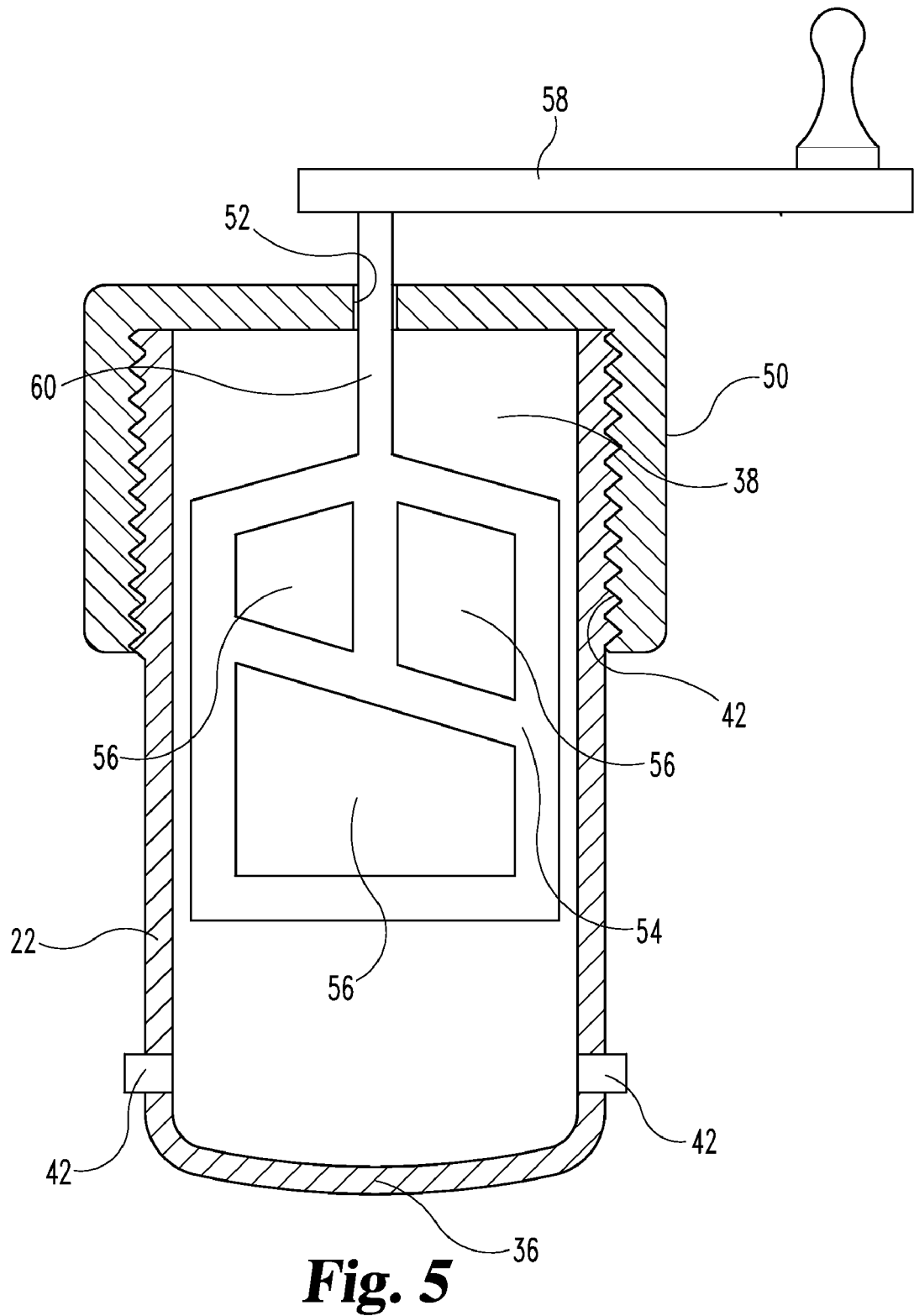
FIG. 5 is a cross-sectional view of the embodiment of a mixing component as shown in FIG. 3.
Figure 6:
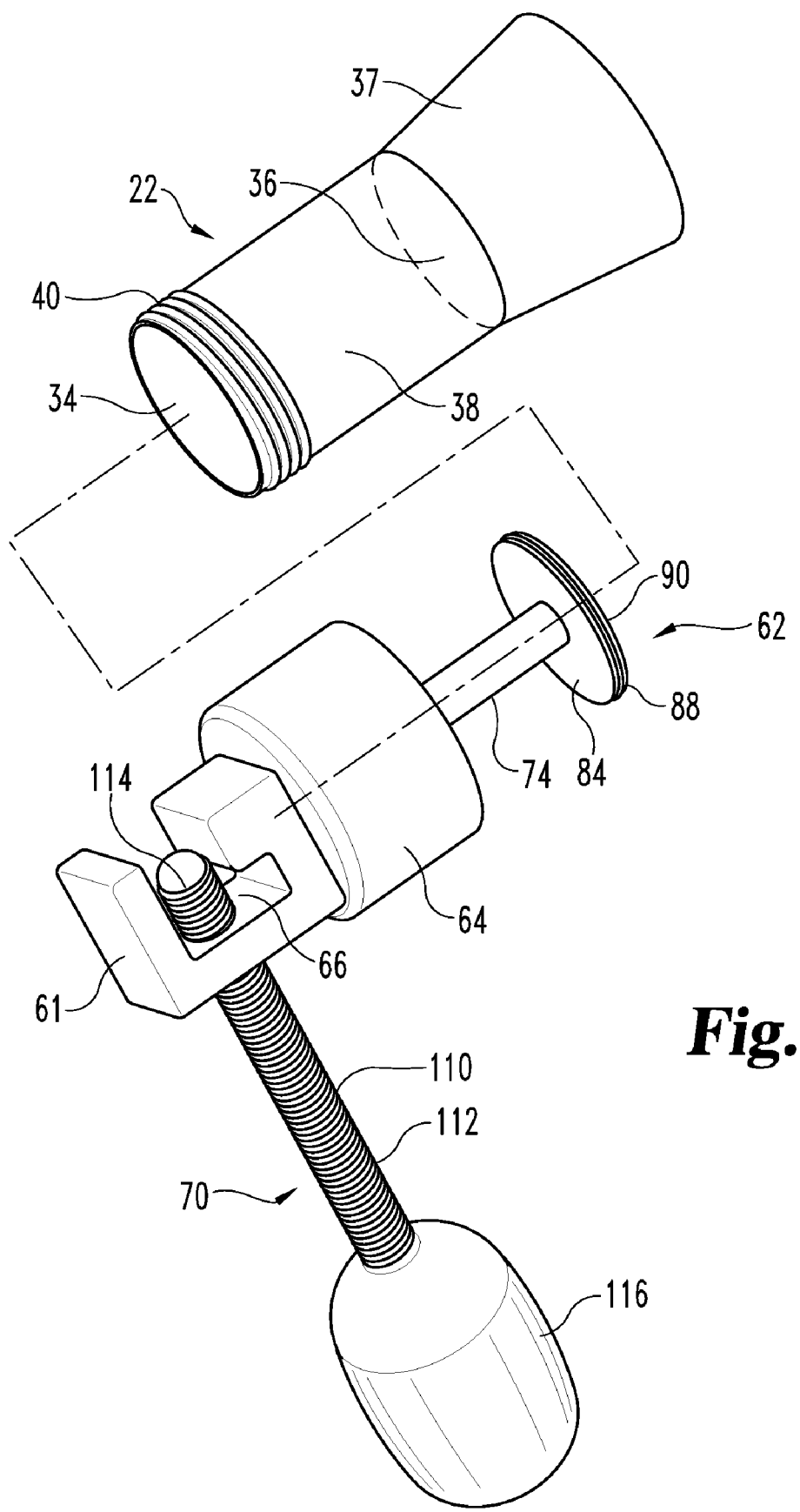
FIG. 6 is an exploded view of a portion of an embodiment of a system for mixing and injecting vertebroplasty compositions as disclosed herein, particularly of the embodiments of a mixing cup as shown in FIG. 1 and of a dispensing component as shown in FIG. 2.
Figure 7:
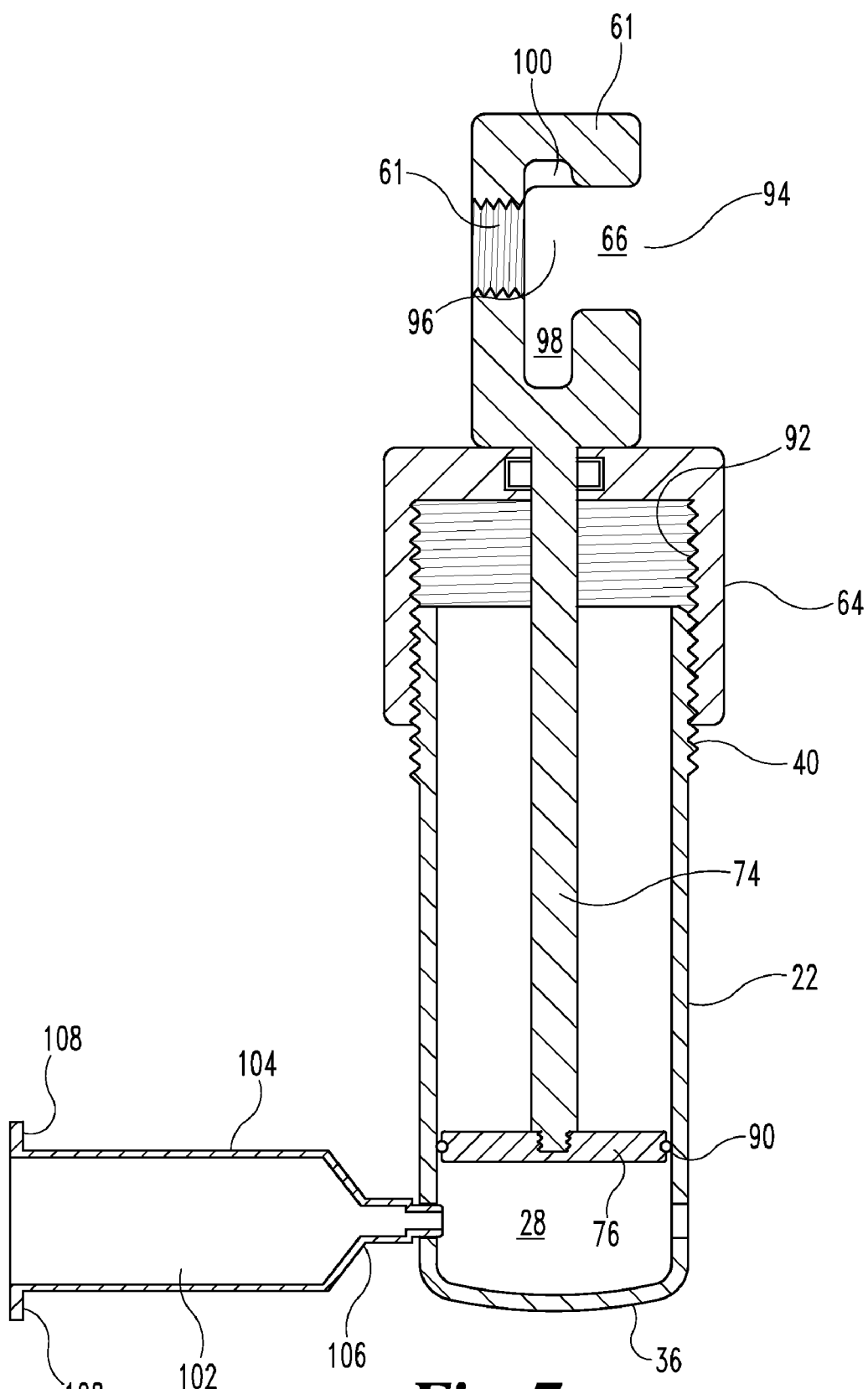
FIG. 7 is a partial cross-sectional view of a portion of an embodiment of a system for mixing and injecting vertebroplasty compositions as disclosed herein, particularly of the embodiments of a mixing cup as shown in FIG. 1 and of a dispensing component as shown in FIG. 2, along with an embodiment of a syringe or injector barrel.

For purposes of promoting an understanding of the principles of the disclosure, reference will now be made to the embodiment illustrated in the drawings and specific language will be used to describe the same. It will nevertheless be understood that no limitation of the scope of the claims is thereby intended, such alterations and further modifications in the illustrated device, and such further applications of the principles of the disclosure as illustrated therein, being contemplated as would normally occur to one skilled in the art to which the disclosure relates.

Referring generally to the drawings, there is shown an embodiment of a system or kit for mixing and injecting a therapeutic composition, such as a cement for use in vertebroplasty. The system or kit includes a mixing cup 22 and a press or dispensing component 24 that operates with mixing cup 22 as further described below. A mixing component 26 is shown in one embodiment that is connectable to mixing cup 22 as part of the system or kit, to assist in preparation of the therapeutic composition.

The illustrated embodiment of mixing cup 22 is a cylindrical body having a wall 32, an open end 34, and a closed end 36 atop a stand 37. Wall 32 and closed end 36 define an internal mixing chamber 38 which communicates with open end 34. Composition components to be mixed together are placed in chamber 38 through open end 34. At or adjacent open end 34 is a thread 40, which in the illustrated embodiment is an external or male thread on wall 32. Thread 40 extends between ¼ and ⅕ of the way along the length of mixing cup 22, in particular embodiments, so that items threaded with thread 40 can travel up to ¼ to ⅕ of the way or more along mixing cup 22 during threading. One or more outlet ports 42 are at or adjacent closed end 36. Port(s) 42 are sized to accommodate the small end of a syringe in a sealing engagement for transfer of the contents of chamber 38 to the syringe, as will be discussed below. A cap or plug 44 is provided for each port 42 so as to prevent the contents of chamber 38 from escaping prior to loading the injector barrel(s).

Mixing component 26 in its illustrated embodiment includes a threaded cap 50 compatible with thread 40 of mixing cup 22. Cap 50 is internally threaded in this embodiment so as to be able to thread with the external embodiment of thread 40. Cap 50 includes a hole 52, which may be centrally located. A paddle 54 in the shape of a planar or undulating figure with a series of openings 56 through it is connected to a handle 58 via a shaft 60. Shaft 60 extends through hole 52, so that turning handle 58 rotates shaft 60 and paddle 54. When cap 50 is threaded with thread 40 of mixing cup 22, paddle 54 is within chamber 38 and in some embodiments is in contact with an interior surface of wall 32 and/or an interior surface of closed end 36 of mixing cup 22. When assembled in that fashion, with cement or other composition components within chamber 38, then turning handle 58 rotates paddle 54 to mix the components into the desired composition.

The illustrated embodiment of press or dispensing component 24 includes a base portion 61 fixed to a first plunger 62, with a threaded cap 64 that is rotatable with respect to plunger 62 in the illustrated embodiment, but in other embodiments may be fixed with respect to plunger 62. Base portion 61 also includes a notch 66 adjoining a threaded hole 68 through which a second plunger 70 extends.

Plunger 62 in this embodiment includes a shaft 74 attached to a disc 76. Shaft 74 is of sturdy metal or plastic and threaded at both ends in this embodiment. A proximal end 78 of shaft 74 is integral with base 61 in this embodiment, while a distal end 80 is threaded into disc 76. It will be understood that the ends of shaft 74 can be alternatively joined to base 61 and/or disc 76. Disc 76 is a short circular cylinder in this embodiment with a central threaded hole 82 into which distal end 80 of shaft 74 is threaded. Disc 76 has an upper surface 84 and an opposed lower surface 86 separated by a circumferential side wall 88. In the illustrated embodiment, the diameter of disc 76 is slightly less than the inner diameter of mixing cup 22, and at least one sealing member 90 is fixed in or on circumferential side wall 88. Sealing member 90 is a bead of malleable material that extends above circumferential side wall 88 and contacts wall 32 of mixing cup 22 to establish a seal yet permit movement of disc 76 along the length dimension of mixing cup 22.

Threaded cap 64 is rotatably attached to base 61 in the illustrated embodiment, as by a tongue-and-groove engagement between cap 64 and the outside of base 61, while in other embodiments cap 64 can be fixed with respect to base 61, as where cap 64 and base 61 are a single piece or monolithic. In an embodiment in which thread 40 of mixing cup 22 is external, the thread 92 of threaded cap 64 is internal or female so that both threads are compatible. The illustrated embodiment of cap 64 has a cylindrical exterior surface so as to present a low profile, although it will be seen that wings, grooves, or other surfaces or textural enhancements may be provided on the exterior surface if needed to assist in turning cap 64 when threading with thread 40.

Figure 8:
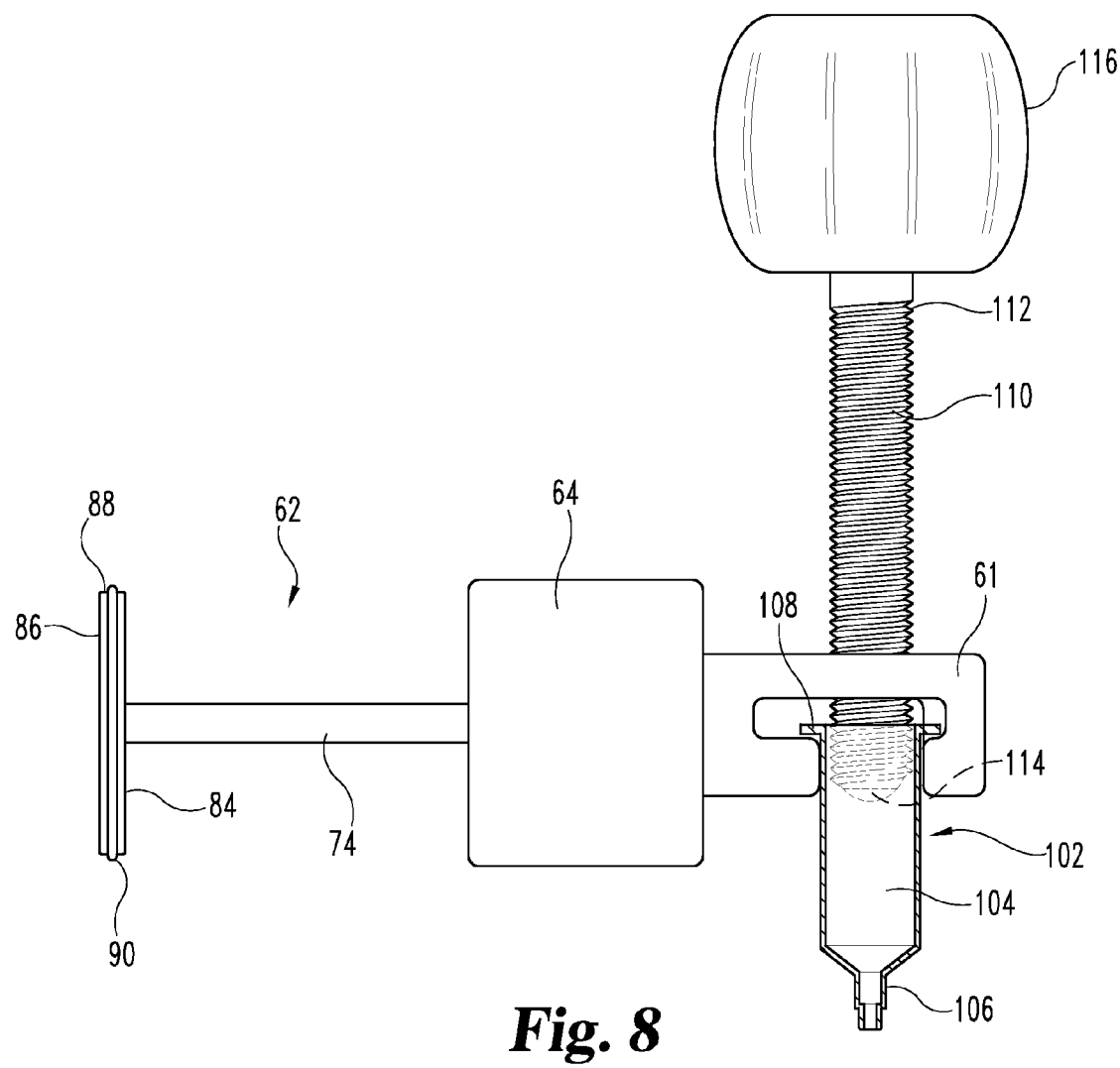
FIG. 8 is a side view of a portion of an embodiment of a system for mixing and injecting vertebroplasty compositions as disclosed herein, particularly of the embodiments of a dispensing component as shown in FIG. 2 and an embodiment of a syringe or injector barrel as shown in FIG. 7.
Figure 9:
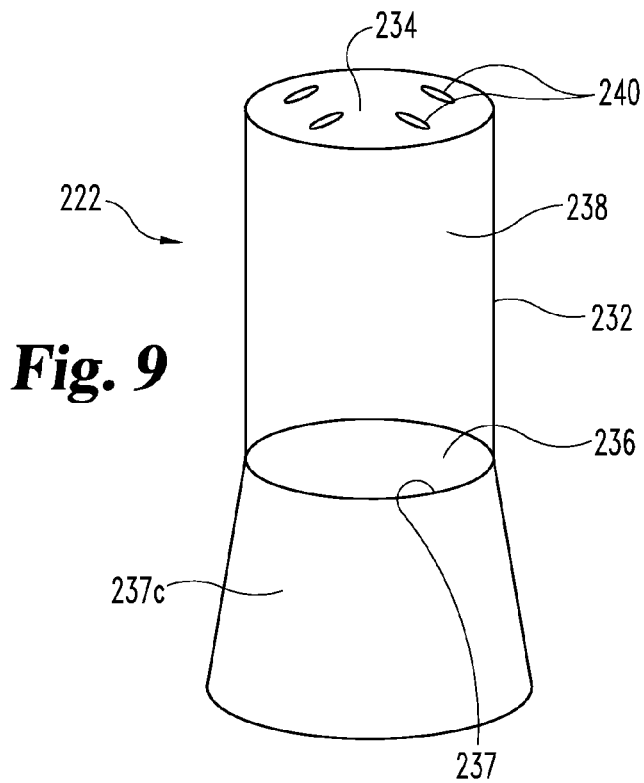
FIG. 9 is a side view of an embodiment of a mixing cup part of an embodiment of a system for mixing and injecting vertebroplasty compositions as disclosed herein.
Figure 10:
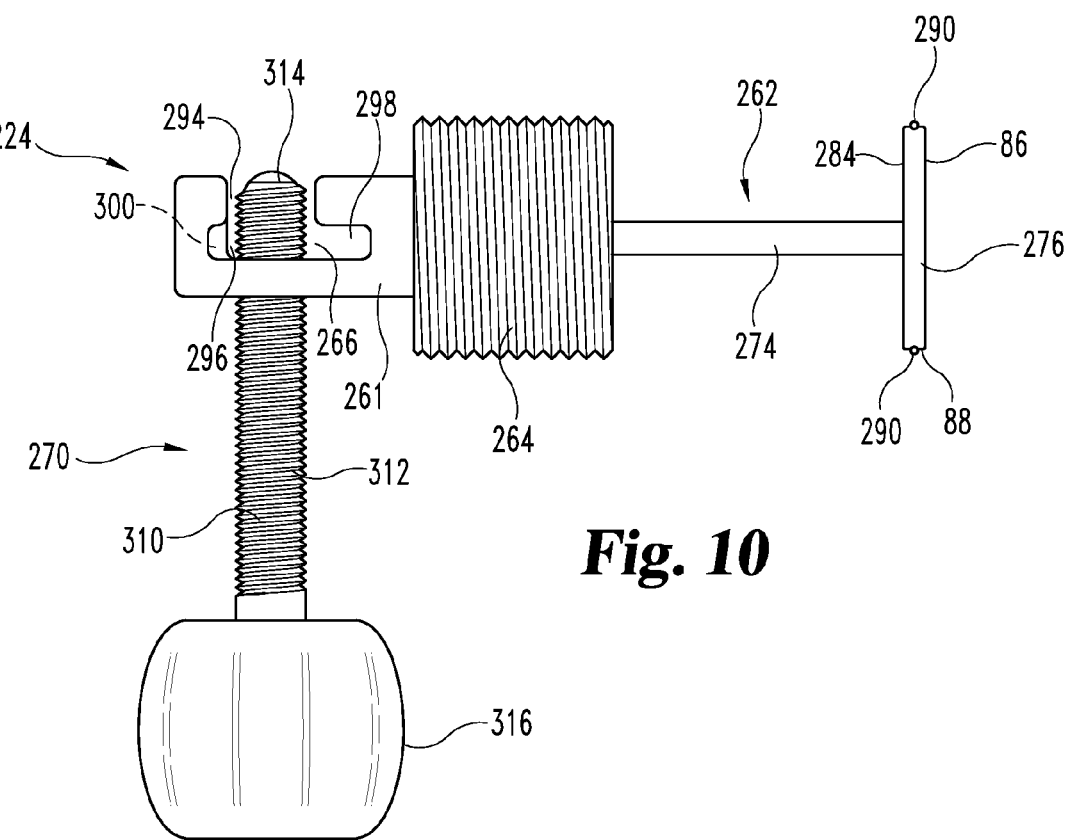
FIG. 10 is a side view of an embodiment of a dispensing component part of an embodiment of a system for mixing and injecting vertebroplasty compositions as disclosed herein.
Figure 11:
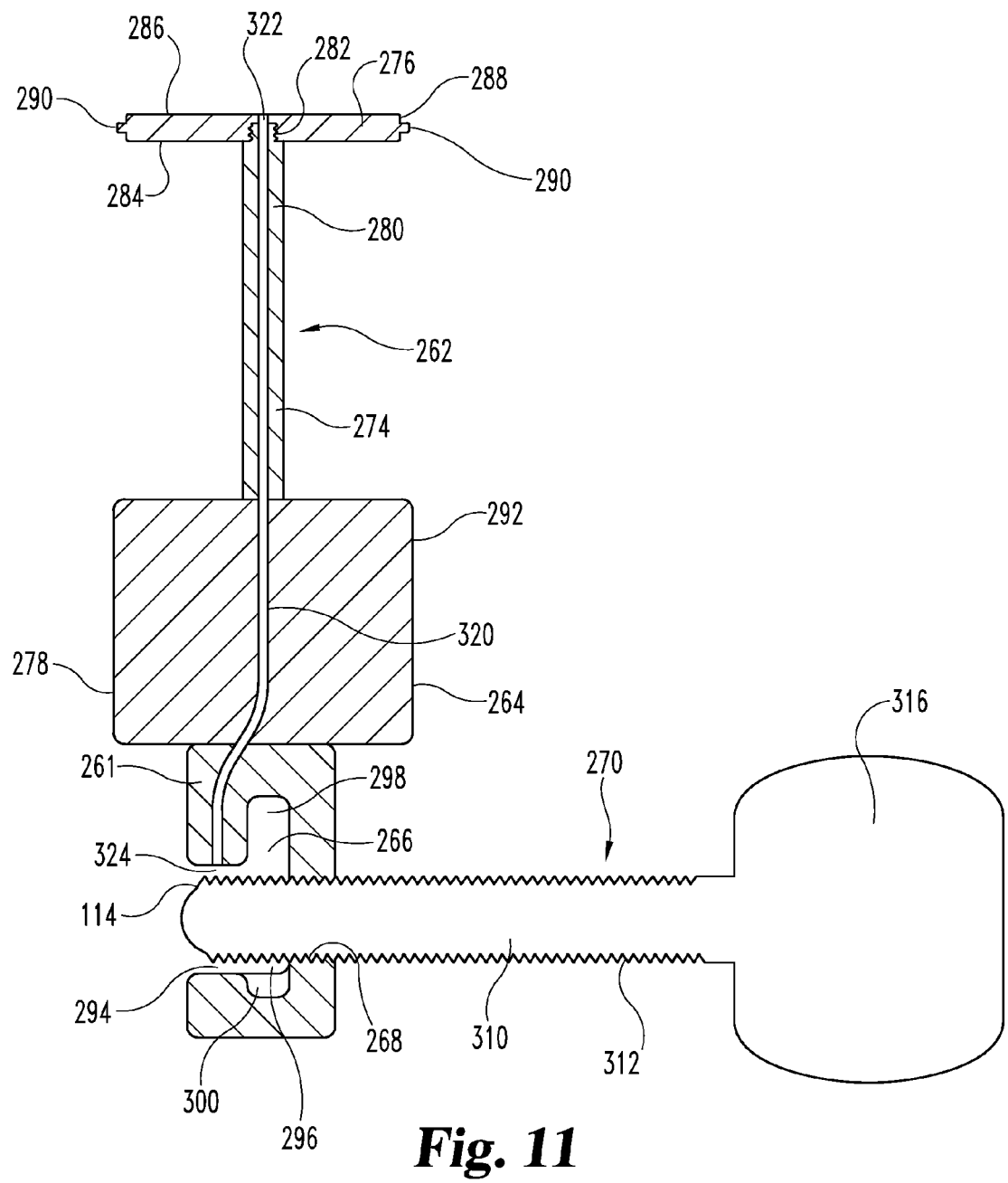
FIG. 11 is a cross-sectional view of the embodiment of a dispensing component as shown in FIG. 10.
Figure 12:
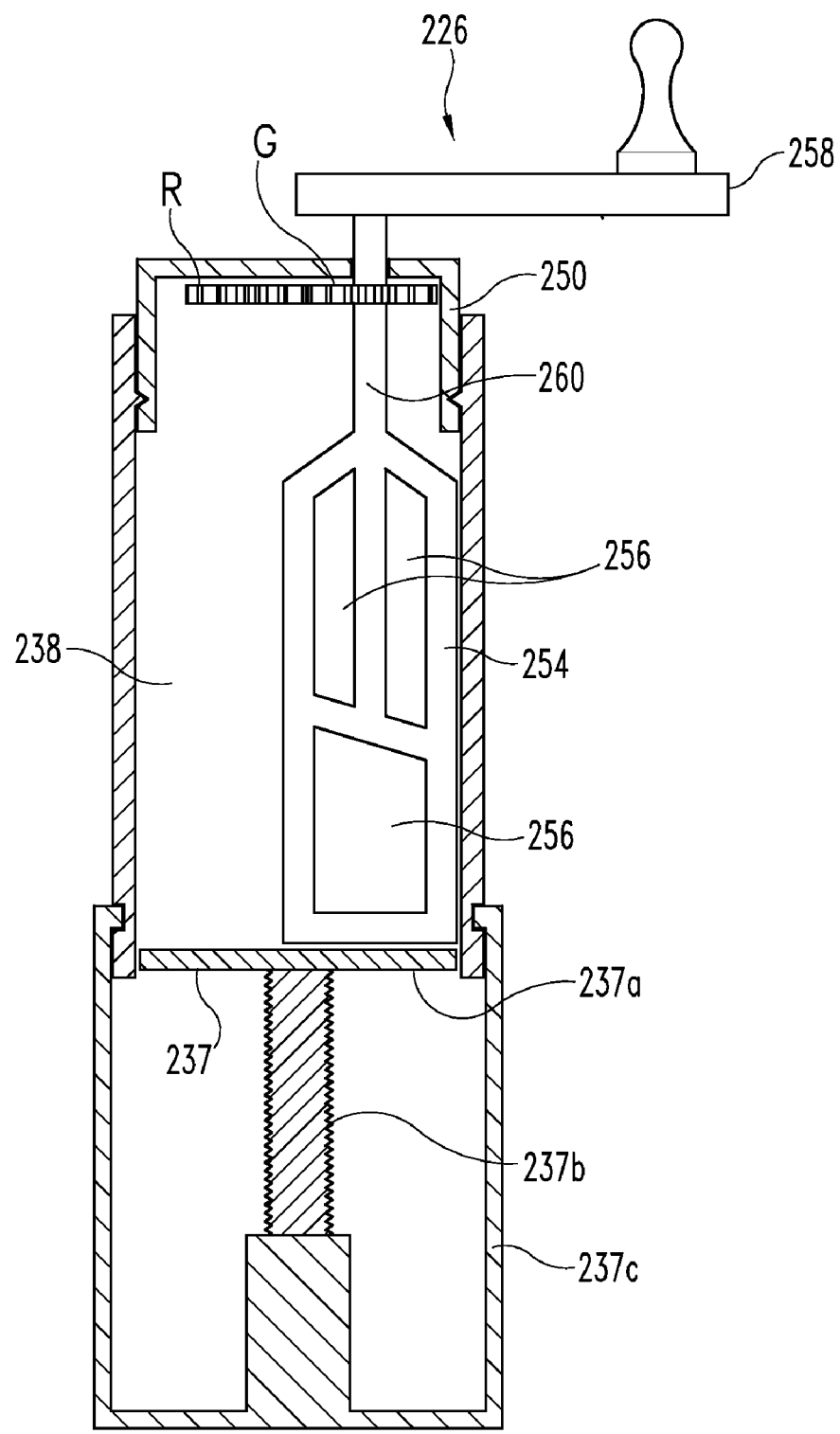
FIG. 12 is a cross-sectional view of an embodiment of a mixing component part of an embodiment of a system for mixing and injecting vertebroplasty compositions as disclosed herein.
Figure 13:
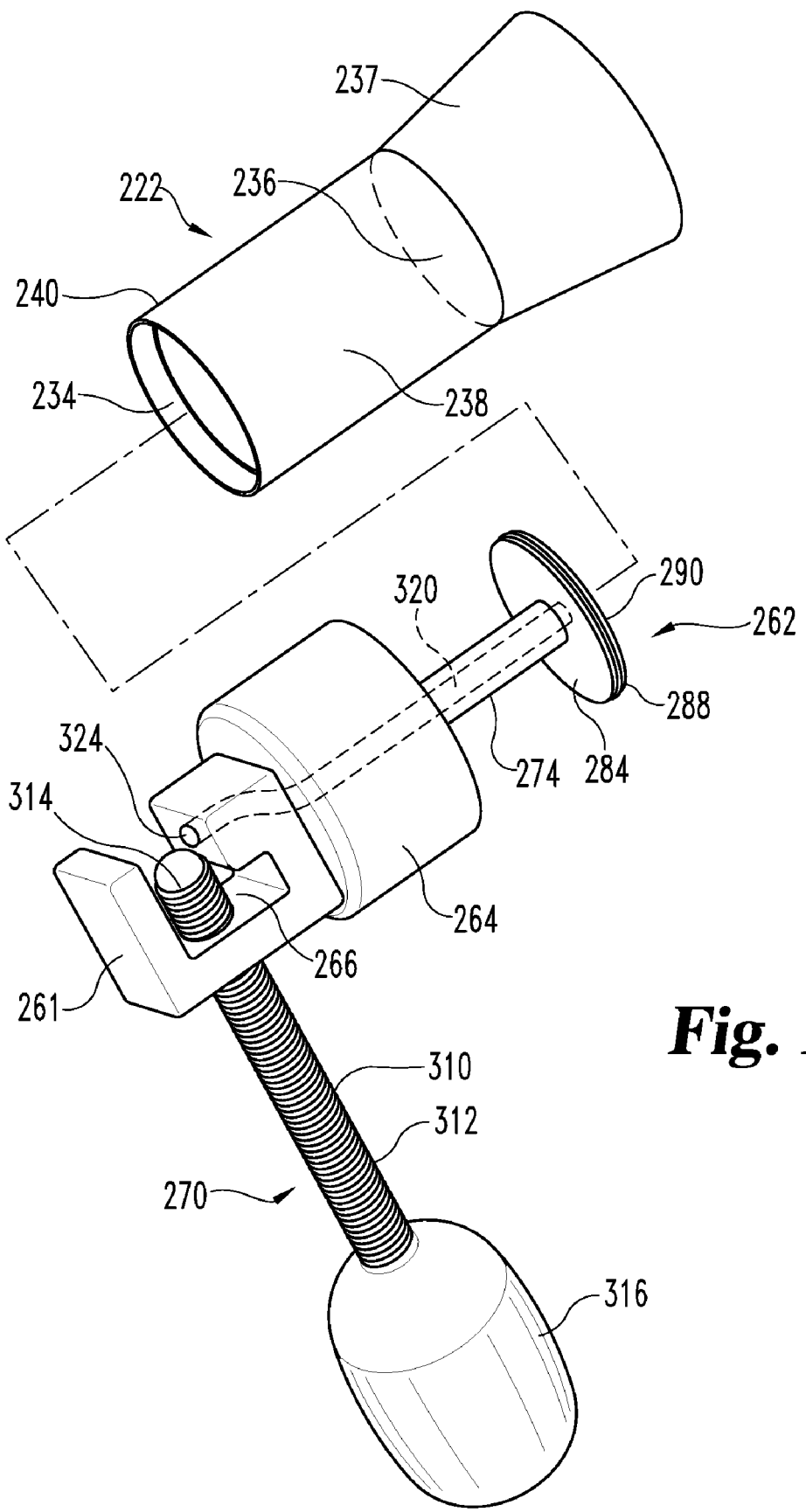
FIG. 13 is an exploded view of a portion of an embodiment of a system for mixing and injecting vertebroplasty compositions as disclosed herein, particularly of the embodiments of a mixing cup as shown in FIG. 9 and of a dispensing component as shown in FIG. 10.
Figure 14:
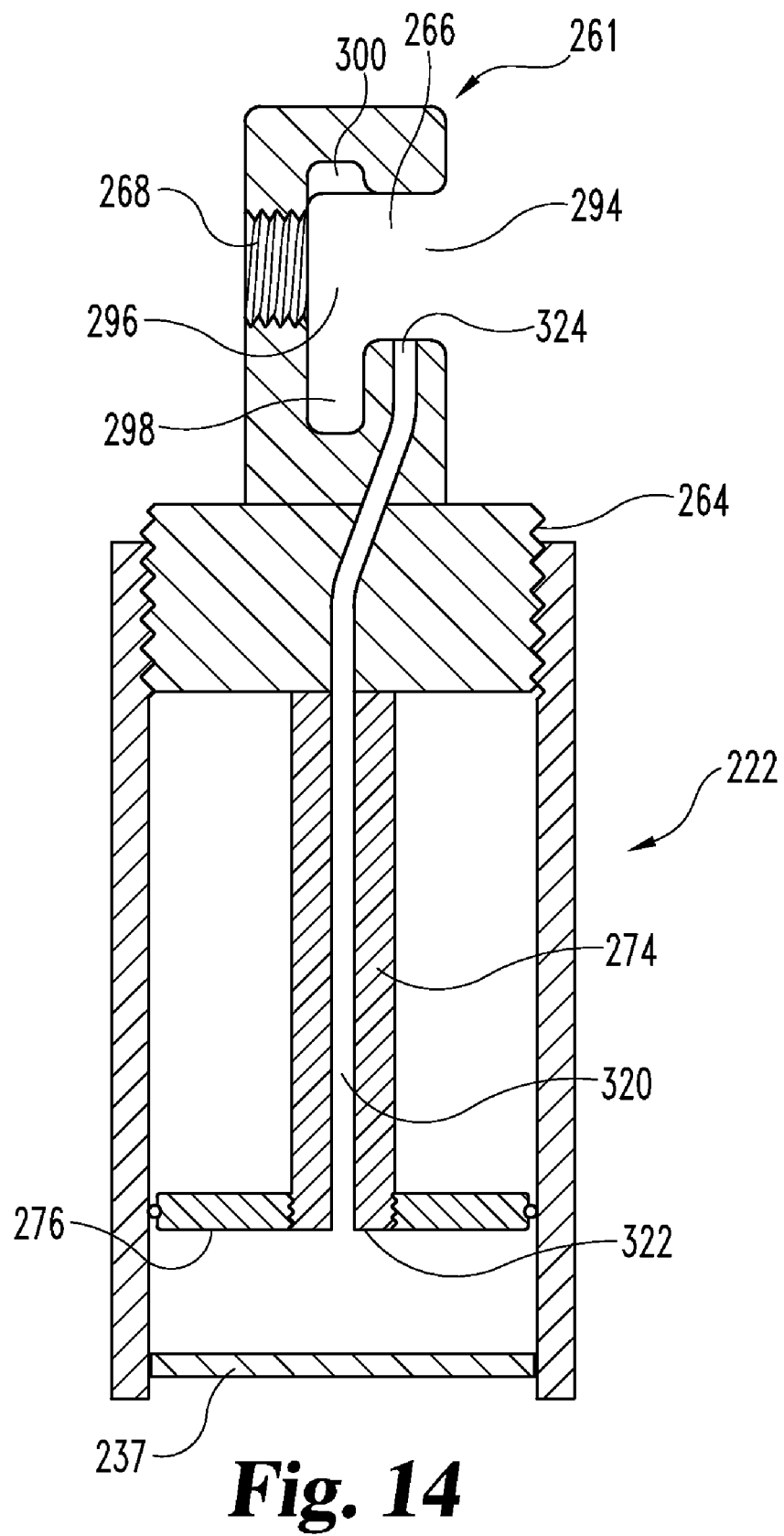
FIG. 14 is a cross-sectional view of a portion of an embodiment of a system for mixing and injecting vertebroplasty compositions as disclosed herein, particularly of part of the embodiment of a mixing cup as shown in FIG. 9 and the embodiment of a dispensing component as shown in FIG. 10, along with an embodiment of a syringe or injector barrel.

Notch 66 is provided in base 61 to accommodate a syringe or injector barrel having one or more upper flanges or lips. Accordingly, notch 66 has an outer space or portion 94 that is the same size as or slightly larger than the outer diameter of the syringe barrel, and a wider inner space or portion 96. Notch 66 as shown has an open side area 98 and an opposed side slot 100, with area 98 and slot 100 being opposing versions of identical features in the illustrated embodiment. An exemplary injector barrel 102 is shown in FIG. 8, and has a cylindrical medial portion 104, a narrower distal tip portion 106, and proximal flanges 108. Notch 66 enables barrel 102 to be securely connected to base 61, where barrel 102 is inserted into notch 66 with flanges 108 oriented substantially perpendicularly or obliquely to a line connecting side area 98 and slot 100. Barrel 102 is then rotated so that respective flanges 108 enter side area 98 and side slot 100 and contact or are adjacent to surfaces of base 61 in side area 98 and slot 100, akin to a bayonet-type connection.

Threaded hole 68 extends through a portion of base 61 to communicate with notch 66 between side area 98 and slot 100 and centered with respect to outer portion 94 of notch 66 in the illustrated embodiment. Hole 68 accepts a threaded shaft 110 of second plunger 70. In addition to threaded shaft 110 and its thread 112, plunger 70 in the illustrated embodiment includes a distal disc or sealing surface 114 and a proximal handle 116. Surface 114 and threaded shaft 110 are sized to be accommodated in an injector barrel (e.g. barrel 102), in a particular embodiment so that surface 114 sealingly engages the inner surface of barrel 102.

In use, dispensing component 24 and mixing component 26 (if used) are initially separate from and unconnected with mixing cup 22. Components for preparing a therapeutic medicament or composition (e.g. a bone cement) are placed into mixing cup 22. As one example, a solid polymer in powder or granulated form is poured into mixing cup 22 (directly or via a funnel (not shown), if necessary) along with or preceded or followed by a liquid monomer. The components are mixed in mixing cup 22. For instance, mixing component 26 is placed on mixing cup 22 with paddle 54 extending into chamber 38 of mixing cup 22. Threaded cap 50 is threaded with thread 40 of mixing cup 22 to secure mixing component 26 and mixing cup 22. Cap(s) or plug(s) 44 should be checked to insure proper secure installation on outlet port(s) 42, to make sure the contents of chamber 38 do not exit during mixing. Handle 58 is turned to rotate paddle 54, thereby mixing the components in chamber 38. Whether mixing is accomplished by paddle 54, or by a stirring rod or another stirring or mixing device or method, mixing continues for a period of time sufficient to adequately mix the components to a generally homogeneous mixture.

When mixing is complete, mixing component 26 or other mixing device is removed from mixing cup 22. Mixing cup 22 and press 24 are then put together by inserting disc 76 of plunger 62 through open end 34 of mixing cup 22. Mixing cup 22 and plunger 62 are moved with respect to each other (with disc 76 moving toward closed end 36 of mixing cup) until thread 40 of mixing cup 22 and thread 92 of cap 64 contact or engage each other. As disc 76 moves along chamber 38, at least sealing member 90 (and perhaps forward face 86) of disc 76 may push quantities of the mixed composition that may have splattered or climbed wall 32 during mixing toward closed end 36. Disc 76 eventually contacts the bulk of the mixed composition that sits at closed end 36. Disc 76 may be advanced to a position such that the mixed composition is packed into closed end 36 to the greatest possible extent. Such a position may be observed (e.g. visually observed through transparent wall 32 or a transparent part of wall 32, if one is present, or tactilely observed via resistance of the mixed composition to disc 76), and/or may be indicated by the turning of threaded cap 64 to the extent needed to place disc 76 at a predetermined distance from closed end 36.

With the composition properly mixed and generally located at or adjacent closed end 36, discharge of the composition can be performed by using plunger 62 to push composition out of outlet port(s) 42. Plug or cap 44 of one or more of the outlet ports 42 is removed, opening a passage through to chamber 38. To the (or each) open outlet port 42 is attached a syringe or injector barrel 102, either by itself (directly) or via a tube or other connector. When all outlet ports 42 are either closed or connected to an injector barrel, threaded cap 64 is turned further to move disc 76 closer to closed end 36, thereby exerting pressure on the mixed composition and forcing at least some of it through outlet port(s) 42 and into attached injector barrel(s) 102. With disc 76 having a significantly greater diameter than that of port(s) 42, a substantial pressure forces composition into injector barrel(s) 102. Injector barrel(s) 102 are filled to the desired extent, e.g. substantially full or with at least enough composition to enable a desired amount of composition to be deposited in or on one or more vertebrae at the vertebroplasty site, even accounting for the volume of any tube or needle between the syringe or injector barrel and the vertebroplasty site. The filling of the injector barrel(s) 102 may be monitored by visual observation of injector barrel(s) 102. Alternatively, threaded cap 64 and/or chamber 38 may be constructed so that a particular number of turns (or part of a turn) of cap 64 corresponds to a particular volume of chamber 38 through which disc 76 passes, and thus a particular volume of composition that is pushed out of chamber 38.

When the desired amount of medicament has been loaded into injector barrel(s) 102, injector barrel(s) 102 are removed from outlet port(s) 42 or their respective connections to outlet port(s) 42. Respective plunger(s) (not shown) are provided for each injector barrel 102, which are then connected directly to a vertebroplasty tube or needle, or to another syringe or injector barrel that is to be connected directly to a vertebroplasty tube or needle. The vertebroplasty tube or needle is placed so that an outlet is in or adjacent to the vertebra(e) to be treated. That placement may occur prior to or after a syringe or injector barrel (e.g. injector barrel 102) loaded with the desired amount of composition is connected to the tube or needle. For example, in some embodiments a needle connected to a tube is first inserted percutaneously or via a different kind of opening into the patient, and maneuvered so that the needle is in or at a vertebra. A loaded syringe or injector barrel is then connected to an end of the tube outside the body, preferably via a high-pressure luer connector. Pressing the plunger on the syringe or injector barrel results in composition exiting the syringe or injector barrel, moving through the tube and exiting the needle into or onto the vertebra, as desired by the physician.

One of the particular problems that can occur during vertebroplasty procedures is the premature curing, hardening or denaturing of the cement composition used in the procedure. To combat that problem, cement compositions have been developed having a solid component and a liquid component (as noted previously) that are only combined immediately before usage. Even with such compositions, delays or errors in combining the components or providing the mixed composition to an injector can result in loss of cement composition or an unsuccessful procedure. By combining the mixing and injecting tasks in one device, fewer steps or structures are needed in the currently disclosed device. It will be understood that mixing cup 22 need not be removed from threaded cap 64 and plunger 62 in order to dispense medicament from an injector barrel 102. In this embodiment, injector barrel 102 can be moved from outlet port 42 directly to notch 66 for dispensing to a vertebroplasty site, eliminating transfer steps, while mixing cup 22 remains connected and/or sealed to cap 64.

A second embodiment of a mixing and dispensing system or kit that further enhances efficiency in preparing and using vertebroplasty composition is shown in FIGS. 9-15. In describing that embodiment, drawing numbers are used that correspond with numbers used for similar or identical features described above, increased by 200. A mixing cup 222 and a press or dispensing component 224 that operates with mixing cup 222 as further described below is provided. A mixing component 226 is shown in one embodiment that is connectable to mixing cup 222 as part of the system or kit, to assist in preparation of the therapeutic composition.

The illustrated embodiment of mixing cup 222 is a cylindrical body having a wall 232, an open end 234, and an opposite end 236 with a movable floor 237. Floor 237 includes a disc 237a with a threaded shaft 237b extending from it, and a knob or handle 237c threaded with shaft 237b and rotatably attached to wall 232 as by a tongue-and-groove connection. In other embodiments, disc 237a may be integral or monolithic with handle or knob 237c, or be fixed in translation but not rotation with respect to handle or knob 237c (as by a tongue-and-groove connection), with knob or handle 237c threaded to cup 222. Wall 232 and disc 237a define an internal mixing chamber 238 which communicates with open end 234. Composition components to be mixed together are placed in chamber 238 through open end 234. At or adjacent open end 234 is a thread 240, which in this embodiment is an internal thread or set of graduated (e.g. discontinuous) ledges inside wall 232. Thread 240 extends far enough along the length of mixing cup 222 so that items threaded with thread 240 are securely connected to mixing cup 222. Turning knob or handle 237c causes disc 237a to move with within wall 232 to expand or reduce the volume of chamber 238.

Mixing component 226 in the illustrated embodiment includes an externally threaded end 250 compatible with thread 240 of mixing cup 222. End 250 is externally threaded in this embodiment so as to be able to thread with the internal embodiment of thread 240. Paddle 254 with openings 256, handle 258, and shaft 260 are essentially identical to corresponding parts of mixing component 26. In this embodiment, a planetary or epicyclic gear system is provided, with a toothed rim R fixed inside end 250 and a sun gear G fixed to handle 258. A planetary gear P is engaged to rim R and sun gear G, and planetary gear P is fixed to shaft 260 and paddle 254. Turning handle 258 rotates sun gear G, turning planetary gear P between sun gear G and rim R, so that gear P rotates around toothed rim R, and paddle 254 is not only rotated around the axis of gear P and shaft 260 but is also moved around mixing cup 222. When end 250 is threaded with thread 240 of mixing cup 222, paddle 254 is within chamber 238 and in some embodiments is in contact with an interior surface of wall 232 and/or an interior surface of floor 237 of mixing cup 222. When assembled in that fashion, with cement or other composition components within chamber 238, then turning handle 258 rotates paddle 254 to mix the components into the desired composition.

The illustrated embodiment of dispensing component 224 includes a base portion 261 of sturdy metal or plastic fixed to a first plunger 262, with a threaded medial part 264 that is fixed or monolithic with plunger 262 and base 261 in the illustrated embodiment, although it could be rotatable with respect to plunger 262 and/or base 261 in other embodiments. Base portion 261 also includes a notch 266 adjoining a threaded hole 268 through which a second plunger 270 extends.

Plunger 262 in this embodiment includes a shaft 274 attached to a disc 276. As already noted, shaft 274 is monolithic with base portion 261 in this embodiment, and is threaded at an end opposite to base portion 261. The threaded end is threaded into disc 276. It will be understood that the ends of shaft 274 can be alternatively joined to base 261 and/or disc 276. Disc 276 is a short circular cylinder in this embodiment with a central threaded hole 282 into which shaft 274 is threaded. Disc 276 has an upper surface 284 and an opposed lower surface 286, which may be planar, conical or concave, or otherwise configured, separated by a circumferential side wall 288. Hole 282 extends from upper surface 284 to lower surface 286, so that the end of shaft 274 inserted in hole 282 is substantially flush with or adjacent lower surface 286. In the illustrated embodiment, the relationship of disc 276 to cup 222 is essentially the same as that described above with respect to disc 76 and cup 22. A sealing member 290 similar or identical to sealing member 90 described above may also be provided.

Threaded medial portion 264 is monolithic or otherwise fixedly attached to base 261 in the illustrated embodiment. In an embodiment in which thread 240 of mixing cup 222 is internal, the thread 292 of threaded end 264 is external or male so that both threads are compatible. Further, where thread 240 is internal, its inner diameter is not greater than the inner diameter of the chamber 238 of cup 222, so that sealing member 290 can pass by thread 240 without interference.

Figure 15:
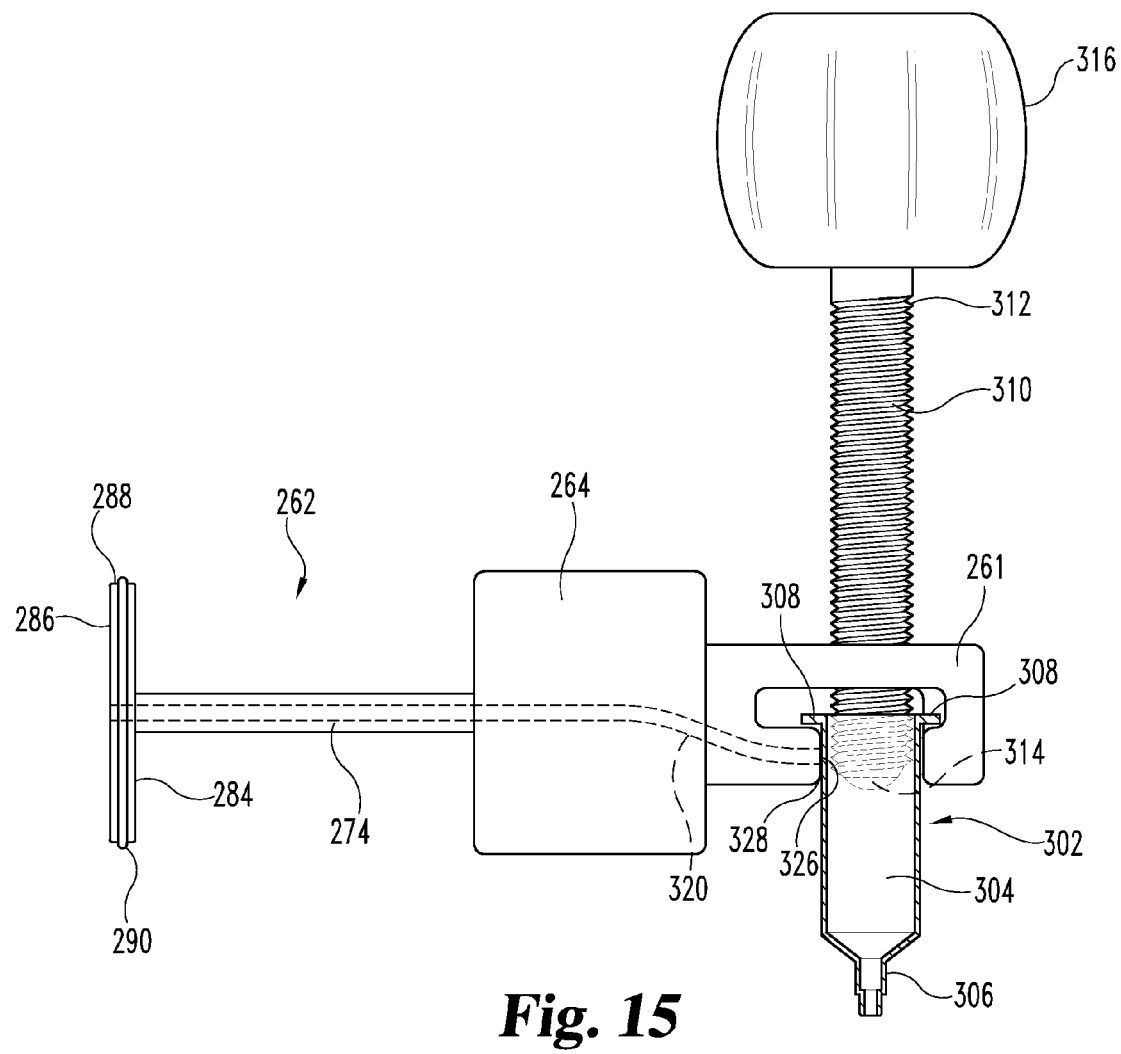
FIG. 15 is a side view of a portion of an embodiment of a system for mixing and injecting vertebroplasty compositions as disclosed herein, particularly of the embodiments of a dispensing component as shown in FIG. 2 and an embodiment of a syringe or injector barrel.

Notch 266 is provided in base 261 to accommodate a syringe barrel or injector barrel having one or more upper flanges or lips. Accordingly, notch 266 has an outer space or portion 294 that is the same size as or slightly larger than the outer diameter of the injector barrel, and a wider inner space or portion 296. In the illustrated embodiment, notch 266 has an open side area 298 and an opposed side slot 300. An exemplary injector barrel 302 is shown in FIG. 15, and has a cylindrical medial portion 304, a narrower distal tip portion 306, and proximal flanges 308. Notch 266 enables barrel 302 to be securely connected to base 261, where barrel 302 is inserted into notch 266 with flanges 308 oriented substantially perpendicularly or obliquely to a line connecting side area 298 and slot 300. Barrel 302 is then rotated so that respective flanges 308 enter side area 298 and side slot 300 and contact or are adjacent to surfaces of base 261 in side area 298 and slot 300, akin to a bayonet-type connection. In other embodiments, it is contemplated that barrel 302 is made integrally with base 261 or otherwise constructed or immovably fixed with base 261.

In this embodiment, a channel or lumen 320 extends from the threaded end of shaft 274 to the notch 266 in base portion 261. A concave or tapered interior end surface 322 of shaft 274 is also provided in the illustrated embodiment which leads into channel 320. Whether tapered, flat, or otherwise configured, end surface 322 is exposed, i.e. unblocked by disc 276. Thus, whether end surface 322 is beyond lower surface 286 of disc 276, flush with surface 286 or within hole 282 of disc 276, end surface 322 and channel 320 are open to access by composition within mixing chamber 238. In other embodiments, a similar concave or tapered surface may be provided on some or all of lower surface 286 of disc 276, which cooperates with or takes the place of surface 322 of shaft 274. This embodiment of channel 320 is along the central axis of shaft 274 and turns or curves in base portion 261 to an outlet 324, which in this embodiment is substantially perpendicular to portion 294 of notch 266.

The size and length of channel 270 is chosen to accommodate the flow characteristics and amount of the composition involved. Accordingly, the diameter of channel 270 is generally small with respect to the diameter of shaft 274, and the length of channel 270 (and thus shaft 274) is generally as small as possible. In the illustrated embodiment, channel 320 has a diameter of about ¼ to ⅛ of the diameter of shaft 274, and the diameter of channel 320 is larger than the inner diameter of the needle inserted into tissue during vertebroplasty (not shown). For ease of transferring the composition, channel 270 should be as large as possible within shaft 274 so as to allow consistent flow of the composition, given that a sufficient amount of composition must move all the way through channel 270 to barrel 302, and a relatively larger channel 270 means a relatively greater amount of composition will remain in channel 270 (and thus cannot enter barrel 302) when floor 237 is moved as much as possible or desired. While the illustrated embodiments of mixing cup 222 (and mixing container 22) generally reflect the sizes of existing similar devices, and thus the dimensions of shaft 274 and the rest of plunger 262 are shown to accommodate those devices, it is to be understood that other sizes may provide better results.

For example, a mixing cup 222 that has about a 1:1 ratio between its internal diameter and its height, along with a plunger 262 (and channel 270) sized to fit in cup 222 as indicated above, provides a shorter length of channel 270 to travel from the bottom of cup 222 to injector barrel 302. Minimizing that length while maintaining pressure from a broad cup 222 into a narrow channel 270 permits sufficient transfer of composition from cup 222 to barrel 320, and minimizes the amount of unusable or wasted composition remaining in channel 270.

A side hole 326 is provided in the medial portion 304 of injector barrel 302, of a size and in a location to at least partially cover outlet 324, and be a part of a sealed or closed passage from channel 320 into injector barrel 302. As will be seen from the drawings, side hole 326 is between a first opening in which second plunger 270 can be inserted and a second tip opening. The illustrated embodiment shows side hole 326 to be substantially perpendicular to the wall of injector barrel 302, and to a longitudinal axis of injector barrel 302. When injector barrel 302 is fitted into notch 266 as described above, opening 326 is adjacent or joining outlet 324 so that composition can travel from channel 320 through outlet 324 and opening 326 and into injector barrel 302. In some embodiments, one or more O-rings or other seals 328 are on one or both of injector barrel 302 and base portion 261 over outlet 324 to present a closed conduit or passage so as to prevent leakage or significant loss of pressure as composition passes through outlet 324 and opening 326, from channel 320 into injector barrel 302. In other embodiments, such as those in which barrel 302 is integral with base 261, such a closed conduit or passage can be formed out of the material(s) of one or both of base 261 and/or barrel 302.

Threaded hole 268 extends through a portion of base 261 to communicate with notch 266 between side area 298 and slot 300 and centered with respect to outer portion 294 of notch 266 in the illustrated embodiment. Hole 268 accepts a threaded shaft 310 of second plunger 270. In addition to threaded shaft 310 and its thread 312, plunger 270 in the illustrated embodiment includes a distal disc or sealing surface 314 and a proximal handle 316. Surface 314 and threaded shaft 310 are sized to be accommodated in an injector barrel (e.g. barrel 302), in a particular embodiment so that surface 314 sealingly engages the inner surface of barrel 302.

In use, press 224 and mixing component 226 (if used) are separate from and unconnected with mixing cup 222. As discussed above with respect to cup 22, components for preparing a therapeutic medicament or composition (e.g. a bone cement) are placed into mixing cup 222 and mixed to a generally homogeneous mixture, as by the use of mixing component 226 or other device or method, as described above.

Following mixing, mixing component 226 (if used) or other mixing device is removed from cup 222, and dispensing component 224 is connected to cup 222 by inserting shaft 274 and disc 276 into chamber 238 of cup 222 and threading or locking medial part 264 of dispensing component 224 to thread 240 of cup 222. With dispensing component 224 fixed with respect to cup 222 in this way, knob or handle 237c of cup 222 is turned to cause disc 237a to move upward or toward disc 276. Forcing disc 237a toward disc 276 moves composition within chamber 238 toward and against disc 276. As knob or handle 237c is further turned, composition is forced into and through channel 320 through shaft 274. Alternatively, forcing shaft 274 further down into chamber 238, as by turning medial part 264 with respect to cup 222, can also provide the force that moves composition through channel 270. Any tapered (e.g. conical) or concave surface that may be present on the lower surface 286 of disc 276 and/or on the end 322 of shaft 274 assists to focus composition toward and into channel 320. Pressure on the composition by turning handle or knob 237c to force floor 237 through chamber 238 is multiplied in the narrower channel 320. The composition is forced through channel 320 and via outlet 324 and opening 326 into injector barrel 302. When a sufficient or predetermined amount of composition has been forced into injector barrel 302, the operator stops turning knob or handle 237c.

Second plunger 270 is then turned to push composition down in and out of injector barrel 302. In some embodiments, plunger 270 is at least partially within injector barrel 302 prior to filling injector barrel 302, so long as plunger 270 does not block opening 326 or impede the filling of injector barrel 302 with composition. As the handle of plunger 270 is turned, plunger 270 forces composition out of injector barrel 302.

Injector barrel 102, 302 is connected via a conduit such as a cannula, flexible tube or similar item (not shown) to a needle (not shown) that is inserted into a vertebra at a location to which the composition is to be deposited. The conduit and needle may be inserted into the patient and connected to injector barrel 102, 302 prior to mixing the composition and/or prior to moving the composition to injector barrel 102, 302. Alternatively, the conduit and needle may be fitted to injector barrel 102, 302 prior to or after mixing and transferring the composition, and then inserted to the vertebroplasty site. Particular embodiments have the conduit and needle placed in the patient ahead of time, then connected to injector barrel 102, 302 after the mixing of the composition and its transfer to injector barrel 102, 302 has occurred. The composition is forced out of injector barrel 102, 302, through the narrow conduit at relatively high pressure and into the vertebra. When injection of the desired amount of vertebroplasty composition has occurred, the needle and/or tube is removed from the patient.

The embodiment of mixing cup 222 and dispensing component 224 further addresses problems noted above that can occur during vertebroplasty procedures. These embodiments not only combine the mixing and injecting tasks in one device, but provide a closed conduit for transferring composition from mixing cup 222 to barrel 302, further limiting the opportunity for the composition to prematurely cure or denature.

It will be understood that features or aspects described with respect to one embodiment above may be included or used with other embodiments. Further, the embodiments of devices described herein are preferably made of sturdy plastics and/or metals (e.g. the shaft of threaded plunger 70, 270) so as to reduce costs and permit simple, straightforward fabrication. Such materials generally make medical devices single-use, since they are relatively inexpensive and can be difficult to clean and sterilize. In use with vertebroplasty compositions such as cements, the nature of the compositions and their curing into a hard, firmly-fixed material suggest that cleaning and sterilizing such devices will be even more difficult. In such single-use applications, for example, injector barrel 302 could be made integral or monolithic with base 261, where no part of dispensing component 224 is deemed reusable. Nevertheless, materials could be used that are less susceptible to fixation of the cured composition and easier to sterilize for some or all of the devices described herein.

While embodiments have been illustrated and described in detail in the drawings and foregoing description, the same is to be considered as illustrative and not restrictive in character, it being understood that only those embodiments have been shown and described and that all changes and modifications that come within the spirit of the disclosure are desired to be protected.

What is claimed is:

1. A system for mixing and dispensing vertebroplasty composition, comprising:
a mixing container having a wall defining a chamber for mixing the composition, said mixing container having a closed end, an open end, and a thread at or adjacent said open end;
an injector barrel for receiving cement dispensed from said container; and
a dispensing component having a base portion, a connecting portion compatible with said thread of said mixing container, a first plunger fixed to said base portion, and a threaded second plunger, wherein when said dispensing component is connected with said mixing container through engagement of said connecting portion with said thread, said first plunger is in said chamber and contacting the interior surface of said wall, and wherein said threaded second plunger is threaded through and rotatable with respect to said handle and insertable into said injector barrel when said injector barrel is connected to said dispensing component.

2. The apparatus of claim 1, wherein said first plunger includes a shaft with first and second ends and a disc, said first end fixed to said base portion and said second end fixed to said disc, wherein said second end has an end surface that is exposed.

3. The apparatus of claim 2, wherein said base portion includes an insertion area to which said injector barrel is connected, and said shaft includes a channel extending from said end surface through said shaft and base portion to said insertion area.

4. The apparatus of claim 3, wherein said injector barrel includes a substantially cylindrical medial portion, said injector barrel having a first opening for accommodating said second plunger, a second opening at a tip portion, and a side hole between said first and second openings.

5. The apparatus of claim 4, wherein when said injector barrel is connected to said insertion area of said base portion, said side opening of said injector barrel communicates with said channel.

6. The apparatus of claim 5, further comprising at least one seal around one or both of said channel and said side hole, whereby leakage between said channel and said injector barrel is minimized.

7. The apparatus of claim 3, wherein said closed end of said mixing container is movable toward said disc of said first plunger when said first plunger is in said mixing container, whereby the composition is forced from said mixing container into said channel.

8. The apparatus of claim 3, wherein when said first plunger is in said mixing container, said disc is movable with respect to said mixing container toward said closed end to force the composition into said channel.

9. The apparatus of claim 3, wherein at least one of said end surface of said shaft and a surface of said disc adjacent said end surface of said shaft is at least partially concave.

10. The apparatus of claim 3, wherein at least one of said end surface of said shaft and a surface of said disc adjacent said end surface of said shaft is at least partially conical.

11. The apparatus of claim 1, wherein said second plunger is oriented substantially perpendicular to said first plunger.

12. The apparatus of claim 1, further comprising a mixing attachment having a thread, a handle, and a paddle attached to and rotatable by said mixing attachment handle, wherein when said mixing attachment is threaded with said thread of said mixing container, said paddle is within said chamber and turning said mixing attachment handle turns said paddle to mix the components of the vertebroplasty composition in said container.

13. The apparatus of claim 1, wherein said mixing container includes at least one outlet port adapted to connect to said injector barrel, and wherein when said injector barrel is connected to said port, said closed end of said mixing container is movable toward said disc of said first plunger, whereby the composition is forced from said mixing container through said outlet portion and into said injector barrel.

14. The apparatus of claim 1, wherein said mixing container includes at least one outlet port adapted to connect to said injector barrel, and wherein when said injector barrel is connected to said port, said disc is movable with respect to said mixing container toward said closed end to force the composition through said outlet port and into said injector barrel.

15. A system for mixing and dispensing a vertebroplasty composition, comprising:
a mixing cup having an external wall, a closed end and an open end, said open end having an external thread, said wall and said closed end forming a mixing chamber for holding and mixing components of the vertebroplasty composition; and
a dispensing component having a base member firmly connectable to said open end of said mixing cup and a plunger fixed with respect to said base member, said plunger having a shaft with first and second ends and a disc, said first end fixed with respect to said base portion and said second end fixed to said disc, wherein said second end has an end surface that is exposed, and wherein said dispensing component includes a channel extending from said end surface of said shaft through said shaft and base member to an outlet in said base member.

16. The system of claim 15, further comprising a mixing component firmly connectable to said mixing cup, said mixing component having an axle, a handle fixed at one end of said axle, and a paddle fixed to the other end of said axle, wherein said paddle is insertable into said mixing chamber of said mixing cup so that lateral edges of said paddle contact said wall of said mixing cup, wherein when the mixing component is firmly connected to said mixing cup and components of the vertebroplasty composition are within the mixing chamber, turning said handle rotates said paddle to mix the components of the vertebroplasty composition.

17. The system of claim 16, further comprising an injector barrel having a first end insertable into said base member and a second tip end, said first end having a first opening that accommodates said second plunger, said second end having a second opening, and wherein said injector barrel has a side hole intermediate said first and second openings that substantially aligns with said channel when said injector barrel is inserted into said base member.

18. The system of claim 17, wherein said closed end of said mixing cup is movable, and wherein when said mixing cup is firmly connected to said dispensing component so that said plunger fixed to said base member is within said mixing chamber, said closed end of said mixing cup is movable toward said disc, so that when vertebroplasty composition is within said mixing chamber and said injector barrel is inserted into said base member, movement of said closed end of said mixing cup toward said disc forces vertebroplasty composition through said channel and into said injector barrel.

19. The system of claim 17, wherein said plunger fixed to said base member is movable with respect to said mixing cup when within said mixing chamber, so that when vertebroplasty composition is within said mixing chamber and said injector barrel is inserted into said base member, movement of said disc toward said closed end of said mixing cup forces vertebroplasty composition through said channel and into said injector barrel.

20. The system of claim 15, wherein said dispensing component includes a second plunger having a threaded shaft threadedly engaged with said base of said dispensing component.

21. The system of claim 20, wherein said first and second plungers are non-parallel.

22. The system of claim 20, wherein said first and second plungers are substantially perpendicular.

23. The system of claim 15, wherein at least one of said end surface and a surface of said disc adjacent said end surface is at least partially concave or conical.

24. The system of claim 15, wherein said dispensing component is threadedly connectable to said thread of said mixing cap.

25. The system of claim 15, wherein the disc is adapted to permit the vertebroplasty composition to pass through said disc only into said channel.

* * * * *